United States Patent [19]
Prieskorn

[11] Patent Number: 6,019,741
[45] Date of Patent: Feb. 1, 2000

[54] ORTHOPEDIC FOOT SPLINT

[76] Inventor: David W. Prieskorn, 10446 Summit View, Brighton, Mich. 48116

[21] Appl. No.: 09/005,140

[22] Filed: Jan. 9, 1998

[51] Int. Cl.[7] .......................................................... A61F 5/00
[52] U.S. Cl. .................................... 602/5; 602/27; 602/28
[58] Field of Search .................................. 602/5, 12, 23, 602/24, 25, 27, 28, 29, 160, 62, 65

[56] References Cited

U.S. PATENT DOCUMENTS

| | | | |
|---|---|---|---|
| 5,219,324 | 6/1993 | Hall | 602/28 |
| 5,503,622 | 4/1996 | Wehr | 602/27 |
| 5,507,720 | 4/1996 | Lampropoulos | 602/27 |
| 5,776,090 | 7/1998 | Bergmann et al. | 602/27 X |

OTHER PUBLICATIONS

The #851 PF Night Foot Sling from Professional Products, Inc. 1997 advertising material.

PF Night Splint advertising material.

Footdrop Braces, Type 670 advertising material.

*Primary Examiner*—Richard J. Apley
*Assistant Examiner*—Kim M. Lee
*Attorney, Agent, or Firm*—Young & Basile, P.C.

[57] ABSTRACT

An orthopedic splint for the treatment of plantar fasciitis and similar disorders has a rigid brace adapted to be worn on the front of the lower leg while leaving the rear of the leg, ankle and heel uncovered. This configuration makes the invention splint comfortable when the patient is laying on his/her back or side, because there is no rigid structure to come between the patient's leg or foot and a mattress or other surface on which the leg may be resting. Alternative embodiments of the invention splint contact either the top or the bottom (dorsal or plantar surfaces) of the foot.

7 Claims, 1 Drawing Sheet

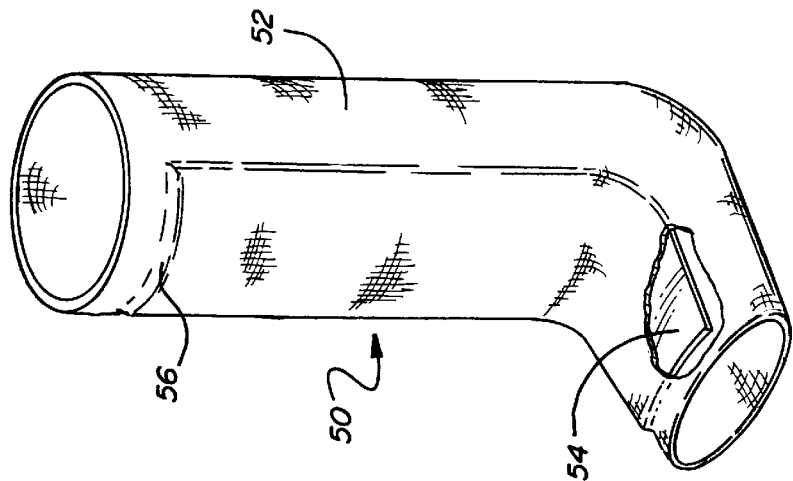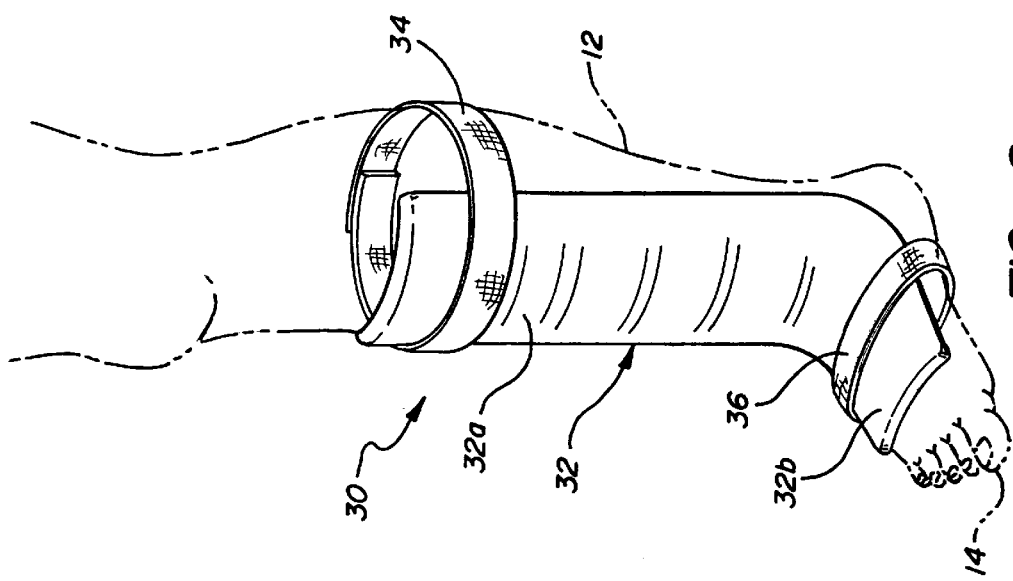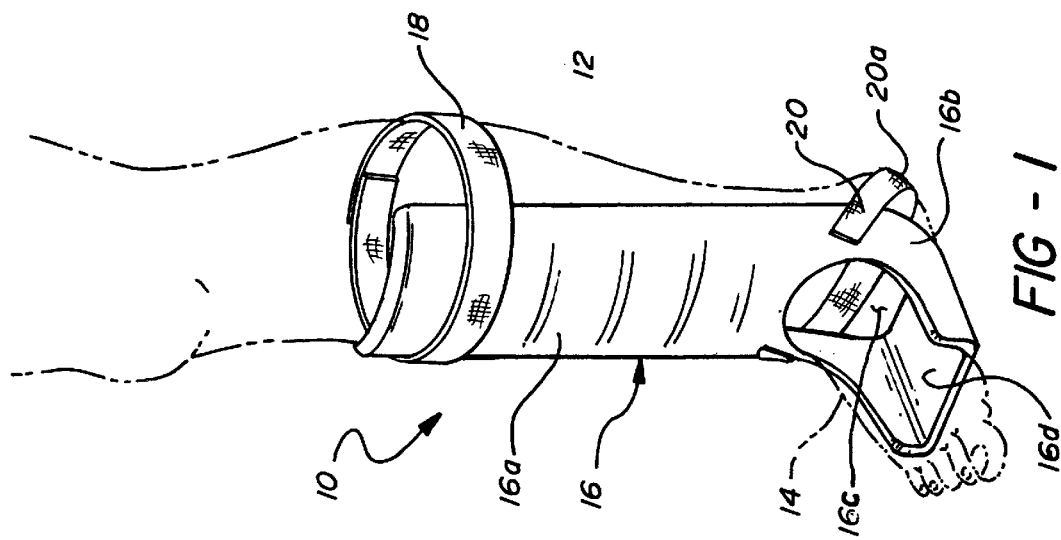

ORTHOPEDIC FOOT SPLINT

FIELD OF THE INVENTION

The present invention relates to a splint to be worn on the lower leg and foot for the treatment of plantar fasciitis, or heel-spur syndrome.

BACKGROUND OF THE INVENTION

Plantar fasciitis is a common problem among people who are active in sports, particularly runners. It is an inflammation of the plantar fascia, the thick tendon on the bottom of the foot which is attached to the heel bone (the calcaneus) and fans forwardly to the toes. The plantar fascia maintains the arch of the foot and is placed in tension during walking and running. Any sport where the foot lands repeatedly, such as running or jogging, can overload the plantar fascia and produce an inflammation, usually at the point where the fascia is attached to the heel bone. The reaction of the heel bone to the inflammation is often to produce spike-like projections of new bone called heel spurs. Both the initial inflammation of the fascia and walking on the heel spurs can cause sharp pain.

A broad range of treatments are prescribed for plantar fasciitis, depending upon the severity of the injury and length of time the condition has existed. Among the commonly used treatments are rest, ice, anti-inflammatory/ analgesic medication, heel pads, taping, physical therapy and surgery.

Another form of treatment for the condition is the wear of a splint or orthosis which maintains the foot in a slightly dorsiflexed condition, so that when viewed from the side the foot and lower leg form an included angle of approximately 85° or less. Typically, such a splint is prescribed for wear at night while the patient is in bed. This maintains a slight stretch of the fascia when it would otherwise be allowed to shorten while the leg and foot muscles are relaxed during sleep. These so-called "night splints" have in the past taken one of two forms.

The first type of prior-art splint consists of a thick, rigid plastic footbed and a pair of rigid plastic bars extending vertically upward on either side of the footbed. A flexible fabric sheath for encircling the foot and leg is also attached to the foot bed, the sheath being open along its front so that the patient may put on the entire appliance like a boot. The footbed underlies the entirety of the patient's foot, and the bars pass along either side of the ankle and lower leg. Straps are attached to the footbed and the bars and are fastened around the foot and lower leg respectively to secure the splint in position and so maintain the patient's foot in the proper, slightly flexed orientation. Such splints are quite heavy and bulky, and it is common for patients to complain that they are uncomfortable and interfere with sleep.

The second type of prior art splint is a generally L-shaped brace made of a relatively thin layer of molded plastic such as polypropylene. The forward-facing surface of the brace is concave to fit around the rear and sides of the patient's calf, ankle and heel. The bottom portion of the "L" extends forwardly beneath the sole of the foot. These splints generally are lined with padding made from a foam or synthetic pile, and are held in place on the lower leg and foot by means of adjustable straps, typically secured with hook-and-pile fasteners. While such splints are less bulky than the first type of prior art splint, some patients still complain that they are uncomfortable, particularly when worn in bed. The rigid portion of the splint contacts the rear and sides of the heel, ankle and lower leg, and so comes between the patient and the bed mattress during most sleeping postures. The splints may be so uncomfortable that patients cannot get a normal night's rest or may discontinue use of the splint before it has achieved the desired therapeutic result.

Another known type of orthopedic device for the treatment of plantar fasciitis is known as a foot sling. The foot sling consists of a wide band of flexible, padded material which encircles the patient's lower leg just below the knee, and a flexible strap which passes beneath the ball of the patient's foot and is secured at its ends to the upper leg band on either side of the leg. The strap is tightened to pull upwardly on the foot and so maintain it in a flexed position. The foot sling may be uncomfortable to some patient's since the upper leg band must be tight enough around the leg to prevent it from slipping downward when the strap is tightened.

SUMMARY OF THE INVENTION

It is an object of the present invention to provide an orthopedic splint for the treatment of plantar fasciitis and similar ailments by maintaining the foot in a slightly flexed position with respect to the lower leg.

It is a further objective to provide a leg splint which is more comfortable than existing splints when worn by a patient in bed or otherwise in a reclined position.

These objectives are achieved by a splint comprising a rigid brace adapted to contact the front of the lower leg while leaving the rear of the leg, ankle and heel uncovered. This configuration makes the invention splint comfortable when the patient is laying on his/her back or side, because there is no rigid structure to come between the patient's leg or foot and a mattress or other surface on which the leg may be resting.

In a first embodiment of the invention, the rigid portion or brace of the splint overlays the front of the lower leg and splits in two adjacent side pieces adjacent its lower end to pass downwardly on either side of the ankle, then passes around the bottom of the foot and extends forward to contact the arch and ball of the foot sole. This embodiment of the invention is preferably secured to the leg by an adjustable strap affixed to the brace adjacent its upper end and which wraps around the rear of the patient's calf. A second strap may be provided which is attached lower on the brace and wraps behind and beneath the heel to hold the foot securely in the splint.

In a second embodiment of the invention, the rigid brace of the splint covers the front portion of the lower leg, extends downwardly over the front of the ankle, and then forwardly along the top of the foot to contact the instep. The brace is secured to the patient's leg by an adjustable strap attached to the brace adjacent its upper end and which is tightened around the rear of the lower leg, and one or more adjustable straps attached to the instep portion of the splint and which are tightened around the bottom of the ball and/or arch of the foot.

In a third embodiment of the invention, the brace portion of the splint has substantially the same geometry as that of the second embodiment, but the brace is secured to the patient's leg and foot by means of an elastic stocking. The brace is sewn into the stocking or otherwise attached thereto such that when the stocking is pulled on over the patient's foot and lower leg the stocking holds the splint securely in position on the front of the lower leg and on the top of the foot.

BRIEF DESCRIPTION OF THE DRAWINGS

FIG. 1 is a perspective view of a first embodiment of the invention splint;

FIG. 2 is a perspective view of a second embodiment of the invention splint; and FIG. 3 is a perspective view of a third embodiment of the invention splint.

DETAILED DESCRIPTION OF THE PREFERRED EMBODIMENT

Referring to FIG. 1, an orthopedic splint 10 according to the present invention is depicted secured to the lower leg 12 and foot 14 of a patient (shown in phantom). The splint 10 comprises a substantially rigid brace 16 and first and second adjustable straps 18,20 attached to the brace and which wrap around the patient's lower leg 12 and foot 14 respectively to hold the brace securely in the desired position. The brace 16 is preferably molded from a thermoplastic material such as polypropylene, and may have padding (not shown) disposed on the inner surfaces which contact the patient's leg and foot. The padding may take the form of a closed-cell foam or a textile pile material.

The upper portion of the brace 16a is shaped to conform to the curvature of the front or shin area of the patient's lower leg 12. The lower end of the shin-contacting portion 16a extends downwardly on both the left and right sides of the patient's ankle to connect to a foot-contacting portion of the brace 16b. The brace 16 thus forms a tunnel 16c through which the patient's foot 14 extends when the brace is worn. The foot-contacting portion 16b comprises a footbed 16d which extends forwardly beneath the sole of the patient's foot 14, contacting and supporting the arch and ball of the foot. For proper treatment of plantar fasciitis, it has been found that the splint 10 should be configured to maintain the foot 14 in dorsiflexion; that is, with an included angle between the foot and the lower leg 12 (when viewed from the side) of approximately 85° or less.

The first strap 18 is attached to the brace 16 adjacent an upper end of the shin-contacting portion 16a and is wrapped around the patient's calf in order to secure the brace in the desired position. The first strap 18 is preferably formed from a synthetic textile material and may be secured by means of a hook-and-pile fastener, thereby providing infinite adjustability over the desired range.

The second strap 20 is attached to the lower end of the shin-contacting portion 16a, and extends downwardly and to the rear to wrap around the patient's heel. The second strap 20 may have a wide or contoured portion to cup the patient's heel and ensure that it does not slip off. In the embodiment of FIG. 1, the second strap 20 has a short slit 20a running along the length of the strap to allow the strap to spread apart and cradle the heel.

Referring now to FIG. 2, a second embodiment of an orthopedic splint 30 according to the present invention is shown secured to a patient's lower leg 12 and foot 14. In this embodiment, a substantially rigid brace 32 is preferably formed from a thermoplastic material and first and second adjustable straps 34,36 are attached to the brace so that the brace may be secured in the desired position. The brace 32 comprises a shin-contacting portion 32a shaped to conform to the front of the patient's lower leg 12, and a foot-contacting portion 32b extending forwardly from the lower end of the shin-contacting portion so as to overlay and contact the top of the patient's foot 14 in the area of the instep. The concave inner surfaces of the brace 32 may be covered with a soft, compliant material such as a low-density synthetic foam in order to improve the fit and comfort of the splint 30.

The first strap 34 is attached to an upper end of the shin-contacting portion of the brace 32a and wraps around the rear of the patient's calf. The second strap 36 is attached to the foot-contacting portion of the brace 32b and wraps around the bottom of the patient's foot 14 in the vicinity of the ball or arch of the foot. As in the first embodiment of the invention, the straps 34,36 are preferably secured by hook-and-pile fasteners in order to provide for a maximum degree of adjustability. If desired, additional straps may be provided on the brace 32 at other locations to hold the brace more securely in position on the patient's lower leg 12 and/or foot 14.

Referring now to FIG. 3, a splint 50 according to a third embodiment of the invention is shown to consist of an elastic stocking 52 which fits over the patient's lower leg and foot (not shown), and a rigid brace 54 contoured to fit over the front of the patient's shin and the top of the instep of the foot in a fashion substantially similar to the brace 32 of the second embodiment of the invention.

The stocking 52 is made of a material containing a relatively high percentage of elastic fibers, such as that used in compression bandages. The brace 54 is secured to the stocking 52 by, for example, sewing it into a pocket. 56 formed in the stocking so that the brace 54 is completely enclosed by the stocking material. Alternatively, the brace 54 may be secured to the stocking 52 by bands which are secured to the stocking and pass over the brace, or by any other method found to be practical.

The splint 50 is pulled on over the patient's foot and lower leg, and the elasticity of the stocking 52 is sufficient to hold the patient's leg and foot in the proper position with respect to the brace 54 without the need for any additional straps.

Each of the three embodiments of the invention disclosed herein may be constructed by custom molding the brace to fit a particular patient. Alternatively, the splints may be manufactured in a range of sizes (small, medium, large, etc.) as necessary to fit most members of the population. Additional fit adjustment may be accomplished by adding padding material to the inside of the brace. For example, if a patient's lower leg requires that a size "large" splint be used, but the patient's foot is too small to properly fit the foot-contacting portion of the "large" splint, padding or spacing material may be added to the inner surface of the foot-contacting portion to achieve a proper fit.

Whereas preferred embodiments of the invention have been illustrated and described in detail, it will be apparent that various changes may be made in the disclosed embodiments without departing from the scope or spirit of the invention.

The invention claimed is:

1. An orthopedic splint securable to a patient's lower leg and foot to substantially immobilize the foot with respect to the lower leg, the splint comprising:

a rigid brace having a first portion for contacting a front portion of the lower leg and a second portion for contacting and supporting the arch and ball portions of a lower surface of the foot, the brace leaving a heel portion of the foot and rear surfaces of ankle and calf portions of the lower leg uncovered, and the brace configured to maintain the foot in a dorsiflexed condition with respect to the lower leg; and means for securing the first portion of the brace to the lower leg.

2. The orthopedic splint according to claim 1 wherein the means for securing the first portion of the brace to the lower leg comprises a strap attached to the first portion of the brace and adapted to pass behind the rear portion of the lower leg.

3. The orthopedic splint according to claim 1 further comprising a strap attached to the brace and adapted to pass around the heel portion of the foot.

4. The orthopedic splint according to claim 1 wherein first and second portions of the brace are connected by first and second extensions which pass along left and right sides of the ankle respectively.

5. An orthopedic splint securable to a patient's lower leg and foot to substantially immobilize the foot with respect to the lower leg, the splint comprising:

first rigid means for contacting a front portion of the lower leg while leaving rear surfaces of ankle and calf portions of the lower leg uncovered;

second rigid means extending from the first rigid means for contacting and supporting the arch and ball portions of a lower surface of the foot while leaving a heel portion of the uncovered, the brace being configured to maintain the foot in a dorsiflexed condition with respect to the lower leg;

means for securing the splint to the patient's lower leg and foot.

6. The orthopedic splint according to claim 5 further comprising means for securing the second rigid means to the foot.

7. The orthopedic splint according to claim 5 wherein the first rigid means and the second rigid means are connected by first and second extensions which pass along left and right sides of the ankle respectively.

* * * * *